(12) United States Patent
Goldberg

(10) Patent No.: US 11,786,495 B2
(45) Date of Patent: Oct. 17, 2023

(54) MEDICINAL PROPERTIES OF TRIETHYL CITRATE

(71) Applicant: Joel Steven Goldberg, Hillsborough, NC (US)

(72) Inventor: Joel Steven Goldberg, Hillsborough, NC (US)

(73) Assignee: Joel Steven Goldberg, Hillsborough, NC (US)

( * ) Notice: Subject to any disclaimer, the term of this patent is extended or adjusted under 35 U.S.C. 154(b) by 26 days.

(21) Appl. No.: 17/526,163

(22) Filed: Nov. 15, 2021

(65) Prior Publication Data

US 2022/0071937 A1   Mar. 10, 2022

(51) Int. Cl.
*A61K 31/194* (2006.01)

(52) U.S. Cl.
CPC .................. *A61K 31/194* (2013.01)

(58) Field of Classification Search
CPC .................................................. A61K 31/194
USPC ....................................................... 514/574
See application file for complete search history.

(56) References Cited

U.S. PATENT DOCUMENTS

| | | | |
|---|---|---|---|
| 9,616,040 | B2 | 4/2017 | Goldberg |
| 2017/0299579 | A1 | 10/2017 | Goldberg |
| 2018/0333379 | A1 | 11/2018 | Goldberg |

OTHER PUBLICATIONS

Medications for Memory, Cognition and Dementia-Related Behaviors [online], [retrieved on Apr. 14, 2023] Retrieved from the Internet, URL: https://www.alz.org/alzheimers-dementia/treatments/medications-for-memory (Year: 2023).*
Park et al., Inhibition of beta-amyloid1-40 Peptide Aggregation and Neurotoxicity by Citrate, 2009, Korean J Physiol Pharmacol, vol. 13: 273-279 (Year: 2009).*
Tong,BC, Calcium signaling . . . therapies, Biochim Biophys Acta Mol Cell Res, 2018 p. 1745-1760.
Goldberg,JS, Atherosclerosis: . . . Treatment Options, Lipid Insights, 2011.p. 17-26.
Lei, Y et al., Efficacy . . . chelating agents, Calcif Tissue Int, 2013, 93: p. 426-435.
Finkelstein,M, Gold,H, Toxicity of Citric Acid Esters . . . Citrate, Toxicology and Applied Pharmacology, 1959, p. 283-298.
Costello, LC, Franklin,RB, Plasma Citrate Homeostasis: . . . in Medicine, HSOA J Hum Endocrinolgy, 2016, p. 12.
De La Torre,JC,Gonzalez-Lima,F, The FDA Approves Aducanumab . . . Questions,J Alzheimers Disease 2021, 82, p. 881-882.

* cited by examiner

*Primary Examiner* — Kristin A Vajda

(57) ABSTRACT

This invention describes the potential benefits of chronic oral administration of triethyl citrate (TEC) for the treatment of Alzheimer's disease and atherosclerosis. Evidence is presented that TEC crosses the blood brain barrier via passive diffusion, and the pharmacologic properties of TEC are distinct from administration of citrate salts. Further clinical trials in animal and human subjects is encouraged.

2 Claims, No Drawings

MEDICINAL PROPERTIES OF TRIETHYL CITRATE

CROSS-REFERENCES TO RELATED APPLICATIONS

None

FEDERALLY FUNDED RESEARCH

Not applicable

BACKGROUND OF THE INVENTION

Calcium deposition is found in Alzheimer's disease in conjunction with plaque formation, and treatment of beta amyloid protein with calcium produces amyloid like aggregates that positive stain with thioflavin T.[1, 2] When treated with varying concentrations of sodium citrate these aggregates dissolve in response to citrate concentration.

Calcium in the form of calcium hydroxyapatite (CaHA) and calcium phosphate (CP) is frequently deposited in human vascular tissue in atherosclerosis. While many believe that these deposits are random, there appears to be some correlation for this finding. CaHA and CP are deposited in areas where there is a breach in the structural integrity of the tissues.[3] This explains calcium deposition in areas where there is weakness of the arterial system, possibly from shear stress, which includes vascular bifurcations in the left main coronary, internal carotid, aortic iliac, and femoral arteries. The deposition of CaHA and CP in injured tissues, areas of inflammation, and areas near tumor formation is well established and may be a response to improve structural tissue integrity.

Calcium Chelation with Citrate

Citrate, a trivalent anion has been shown to decrease bone calcium in a model of spinal stenosis.[4] The chelation of calcium which includes calcium ions, CaHA and CP is non enzymatic and spontaneous at biologic pH and temperature. Citrate from TEC hydrolysis has significant therapeutic advantages over EDTA, a commonly administered drug to chelate calcium, because it is less toxic and can be administered orally. [5]

Triethyl Citrate

Triethyl citrate (TEC) is used in food preparations to increase the stability of egg white foam and in skin care products. It is a known nontoxic plasticizer. TEC is easily and cheaply synthesized from citric acid and ethanol by Fisher esterification and many modifications to increase the yield and purity of this synthesis have been reported. TEC is well absorbed from the gastrointestinal (GI) tract and is hydrolyzed to ethanol and citrate. The $LD_{50}$ in a 70 kg man is estimated at 500 cc which is extrapolated from animal models.[6] Chronic administration of TEC for eight weeks in animals at a dose of 0.25 cc/kg per day had no effect on weight, blood nitrogen or EKG. At this chronic dose, some weakness and ataxia was observed in the treated animals but normal recovery occurred within 1-4 days after the treatments were discontinued. No evidence of neuromuscular conduction block was observed in TEC poisoned animals and there were no reports of tetany. [6] These data suggest that chronic administration of TEC may be a good drug candidate for decreasing the calcium concentration in the brain with resolution and prevention of plaques in Alzheimer's disease and in resolution and prevention of atherosclerosis in humans.

DRAWINGS

None

DETAILED DESCRIPTION OF THE INVENTION

TEC has many drug characteristic that can be exploited for the treatment of Alzheimer's disease and atherosclerosis. TEC is well absorbed from the GI tract, slowly hydrolyzed to citrate and ethanol in the plasma, crosses the blood brain barrier (BBB), and is likely hydrolyzed in the central nervous system (CNS).

Esterases that can hydrolyze TEC are ubiquitous in the human plasma and cerebral spinal fluid. Esterases in the plasma do not completely hydrolyze many drugs that eventually cross the BBB and these drugs can be active in the CNS. Examples of these esters drugs which are incompletely metabolized by plasma esterases and subsequently cross the CNS as esters include 2-chloroprocaine, cocaine, and heroin. Experimental evidence supports TEC as a CNS drug since it passively crosses the vitelline membrane, a model of the BBB, in contrast to citrate from salts which cross the BBB through monocarboxylate transporters.[7] TEC is hydrolyzed into citrate and ethanol in the CNS both of which are "familiar" to the CNS. Compounds that are familiar to the CNS have known CNS toxicities, and they are more likely to be approved for use as drugs in humans.

The ester hydrolysis of TEC to produce citrate is not pharmacologically identical to administration of citrate salts such as sodium, potassium or magnesium citrate. Citrate salts in solution at biologic pH are basic, but ester hydrolysis of TEC is acidic in solution at biologic pH. Furthermore, citrate feedback mechanisms which are quite complicated involving parathyroid hormone, vitamin D, and renal clearance are not expected to affect citrate levels from TEC in the same manner as those that affect citrate salts.[8] Supporting this proposition, TEC administration in animal models did not result in hypocalcemia, unlike administration of citrate salts to humans. Since TEC in vivo pharmacology, including crossing the BBB, is distinctly from citrate salts, it is unlikely and not obvious that the pharmacologic activity of TEC will mimic the pharmacologic activity of citrate salts. The use of TEC as a drug to treat Alzheimer's disease and atherosclerosis is novel with no reports of such in the world literature.

TEC as a Treatment for Alzheimer's Disease

Senile plaques cause by precipitation of amyloid beta amyloid protein are a hallmark of Alzheimer's disease. It has been shown that calcium precipitates amyloid beta protein into amyloid plaques that stain with thioflavin T, and this precipitation is not a common occurrence when proteins are treated with calcium.[1] At the present time there are no exceptional treatments for Alzheimer's disease, but aducanumad inhibits plaque formation has been approve by the FDA for treatment of this illness.[9] TEC administered orally or parenterally will cross the BBB, be hydrolyzed into citrate and ethanol by CNS esterases, and chelate calcium in the CNS, thereby resulting in dissolution and decrease formation of amyloid plaques in patients who suffer from Alzheimer's disease. Previous work that describes the toxicity of TEC in animal models support the chronic use of TEC in clinical trials for the treatment of Alzheimer's disease.

TEC as a Treatment for Atherosclerosis

Periarterial calcium deposition in the form of CaHA and CP are hallmarks of atherosclerosis. These substances are commonly imaged in calcium computer tomography scanning and reported as a calcium score which is a very good predictor of subsequent coronary artery disease and myocardial infarction. The same process of CaHA and CP deposition is found in other vascular sites in the human body. Citrate has been shown to dissolve CaHA and CP in bone though chelation of calcium, a chemical reaction that is spontaneous under biologic conditions. TEC is hydrolyzed to citrate and ethanol in the plasma and the citrate will dissolve CaHA and CP located in the arterial vessels alleviating the symptoms of vascular insufficiency. Previous work that describes the toxicity of TEC in animal models support the chronic use of TEC in clinical trials for the treatment of atherosclerosis.

Experimental Section

Quail eggs were decalcified by soaking in white vinegar for 24 hours and then washed. The eggs were soaked in phosphate buffered saline (PBS) solutions of 1.0M TEC, 0.1M TEC, and 0.01M TEC in and PBS control for 12 hours. The eggs were then frozen. The albumen and the yolk were easily separated from the frozen eggs by shaving the albumen with a razor blade. The albumen melts at a lower temperature than the yolk which easily facilitated this process. The frozen yolks were washed with water which easily removes the vitelline membrane after which the yolks were tasted by the inventor. The easily distinguishable bitter taste of TEC was perceived in the 1.0M TEC and 0.1M TEC incubated eggs but not in the eggs incubated with 0.01M TEC or PBS. (Table 1) The pH values for aqueous solutions of the dissolved yolks in TEC and control were 4.35, 4.37, 4.34 and 4.35 for 1.0M, 01.M, 0.01M, and PBS respectively.

TABLE 1

TEC permeability in vitelline membrane model of BBB

| Sample (eggs) | Albumen | Yolk | PBS without eggs |
| --- | --- | --- | --- |
| PBS (control) | Not bitter (sour) | Not bitter | Not bitter |
| 1.0M | Moderate bitter | Mild bitter | Very bitter |
| 0.1M | Moderate bitter | Mild bitter | Moderate bitter |
| 0.01M | Not bitter | Not bitter | Not bitter |

Conclusion: TEC in PBS at a concentration of 0.1M or greater crosses the vitelline membrane which is a model of the human BBB.

Lipinski criteria for probable CNS drug like activity compared to TEC is listed in Table 2. Three out of four criteria are met for TEC as a CNS drug.

TABLE 2

TEC vs. Lipinski Criteria for CNS drug like properties

| | TEC | Lipinski Criteria |
| --- | --- | --- |
| Molecular Weight (Da) | 276 | <400 |
| LogP | 1.27 | <5 |
| Hydrogen Bond Donors | 0 | <3 |
| Hydrogen Bond Acceptors | 8 | <7 |

BENEFITS TO SOCIETY

The chemical properties of TEC highly suggest that this drug can chelate calcium in the central nervous system and in the circulatory system. Chronic administration of TEC is well tolerated in animal models. Alzheimer's disease and atherosclerosis are two devastating illness that plague humans with no present day exceptional treatments. Additional animal models and clinical trials of TEC are encouraged because this drug could ameliorate the symptoms of these two conditions.

REFERENCES

1. Goldberg, J. S., CITRATE DISSOLUTION OF BETA-2-MICROGLOBULIN AND AMYLOID BETA PEPTIDE (1-40) AGGREGATES US 2018/0333379 A1, 2018.
2. Tong, B. C., et al., *Calcium signaling in Alzheimer's disease & therapies*. Biochim Biophys Acta Mol Cell Res, 2018. 1865(11 Pt B): p. 1745-1760.
3. Goldberg, J. S., *Atherosclerosis: Viewing the Problem from a Different Perspective Including Possible Treatment Options*. Lipid Insights, 2011. 4: p. 17-26.
4. Goldberg, J. S., CITRATE RESORPTION OF BONE AS A TREATMENT FOR SPINAL STENOSIS U.S. Pat. No. 9,616,040 B2, 2017.
5. Lei, Y., et al., *Efficacy of reversal of aortic calcification by chelating agents*. Calcif Tissue Int, 2013. 93(5): p. 426-35.
6. Finkelstein, M., Gold, H., *Toxicology of Citric Acid Esters: Tributyl Citrate, Acetyl Tributyl Citrate, Triethyl Citrate, and Acetyl Trethyl Citrate*. Toxicology and Applied Pharmacology, 1959. 1: p. 283-298.
7. Goldberg, J. S., VITELLINE MEMBRANE AS A MODEL OF THE BLOOD BRAIN BARRIER US 2017/0299579 A1, 2017.
8. Costello, L. C. and R. B. Franklin, *Plasma Citrate Homeostasis: How It Is Regulated; And Its Physiological and Clinical Implications. An Important, But Neglected, Relationship in Medicine*. HSOA J Hum Endocrinol, 2016. 1(1).
9. de la Torre, J. C. and F. Gonzalez-Lima, *The FDA Approves Aducanumab for Alzheimer's Disease, Raising Important Scientific Questions*1. J Alzheimers Dis, 2021. 82(3): p. 881-882.

Having describe my invention, I claim:

1. A method of treating Alzheimer's disease in a subject comprising administering to said subject a composition comprising triethyl citrate or a prodrug thereof.

2. A method of dissolving an amyloid β peptide aggregate within a brain in a subject comprising administering to said subject a composition comprising triethyl citrate or a prodrug thereof.

* * * * *